(12) United States Patent
Warner et al.

(10) Patent No.: US 9,517,219 B2
(45) Date of Patent: Dec. 13, 2016

(54) TOPICAL DAPSONE AND DAPSONE/ADAPALENE COMPOSITIONS AND METHODS FOR USE THEREOF

(71) Applicant: Allergan, Inc., Irvine, CA (US)

(72) Inventors: Kevin S. Warner, Anaheim, CA (US); Ajay P. Parashar, Fairfax, VA (US); Vijaya Swaminathan, San Francisco, CA (US); Varsha Bhatt, San Francisco, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/885,805

(22) Filed: Oct. 16, 2015

(65) Prior Publication Data
US 2016/0030580 A1    Feb. 4, 2016

Related U.S. Application Data

(62) Division of application No. 14/082,955, filed on Nov. 18, 2013, now Pat. No. 9,161,926.

(60) Provisional application No. 61/728,403, filed on Nov. 20, 2012, provisional application No. 61/770,768, filed on Feb. 28, 2013.

(51) Int. Cl.
| | |
|---|---|
| *A61K 31/136* | (2006.01) |
| *A61K 31/192* | (2006.01) |
| *A61K 9/00* | (2006.01) |
| *A61K 31/145* | (2006.01) |
| *A61K 47/32* | (2006.01) |
| *A61K 47/10* | (2006.01) |
| *A61K 47/14* | (2006.01) |
| *A61K 47/18* | (2006.01) |
| *A61K 47/34* | (2006.01) |

(52) U.S. Cl.
CPC .......... *A61K 31/192* (2013.01); *A61K 9/0014* (2013.01); *A61K 31/136* (2013.01); *A61K 31/145* (2013.01); *A61K 47/10* (2013.01); *A61K 47/14* (2013.01); *A61K 47/183* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 5,532,219 | A * | 7/1996 | McGeer | A61K 31/145 514/42 |
| 5,863,560 | A | 1/1999 | Osborne | |
| 5,989,571 | A * | 11/1999 | Santa | A61K 9/12 424/401 |
| 6,060,085 | A | 5/2000 | Osborne | |
| 6,620,435 | B1 | 9/2003 | Osborne | |
| 7,531,694 | B2 | 5/2009 | Villa et al. | |
| 8,586,010 | B2 * | 11/2013 | Garrett | A61K 8/46 424/59 |
| 9,161,926 | B2 * | 10/2015 | Warner | A61K 9/0014 |
| 2006/0204526 | A1 | 9/2006 | Lathrop et al. | |
| 2010/0029781 | A1 | 2/2010 | Morris | |
| 2010/0130613 | A1 | 5/2010 | Dreno | |
| 2012/0064144 | A1 * | 3/2012 | Benhamou | A61K 9/7023 424/443 |

FOREIGN PATENT DOCUMENTS

| | | |
|---|---|---|
| WO | WO 2009/061298 A1 * | 5/2009 |
| WO | 2009-108147 | 9/2009 |
| WO | WO 2009/108147 A1 * | 9/2009 |
| WO | WO 2010/105052 A1 * | 9/2010 |
| WO | WO2010105052 A1 | 9/2010 |
| WO | WO2011-014627 | 2/2011 |
| WO | WO 2011/014627 A1 * | 2/2011 |

OTHER PUBLICATIONS

Draelos, Zoe D. et al., Two Randomized Studies Demonstrate the Efficacy and Safety of Dapsone Gel, 5% for the Treatment of Acne Vulgaris, Journal of American Academy of Dermatology, Mar. 2007, 26 Pages, 56, US.
Lubrizol (Online). "Viscosity of CARBOPOL Polymers in Aqueous Systems". (Retrieved Mar. 18, 2014). Retrieved from the Internet<URL:http://www.lubrizol.com/Life-Science/Documents/Pharmaceutical/Technical-Data-Sheets/TDS-730-Viscosity-Carbopol-in-Aqueous-Systems.pdf>.
Notification of Transmittal of the International Search Report and the Written Opinion of the International Searching Authority, or the Declaration, International Application No. PCT/US2013/070613, International Filing Date, Nov. 18, 2013, Date of Mailing Feb. 12, 2014.

* cited by examiner

*Primary Examiner* — Leslie A. Royds Draper
(74) *Attorney, Agent, or Firm* — Laura L. Wine

(57) ABSTRACT

Dapsone and dapsone/adapalene compositions can be useful for treating a variety of dermatological conditions. The compositions of this disclosure include dapsone and/or adapalene in a polymeric viscosity builder. Subject compositions can be adjusted to optimize the dermal delivery profile of dapsone to effectively treat dermatological conditions and improve the efficiency of pharmaceutical products applied to the skin. Use of the polymeric viscosity builder provides compositions with increased concentrations of diethylene glycol monoethyl ether relative to compositions without the polymeric viscosity builder.

8 Claims, 3 Drawing Sheets

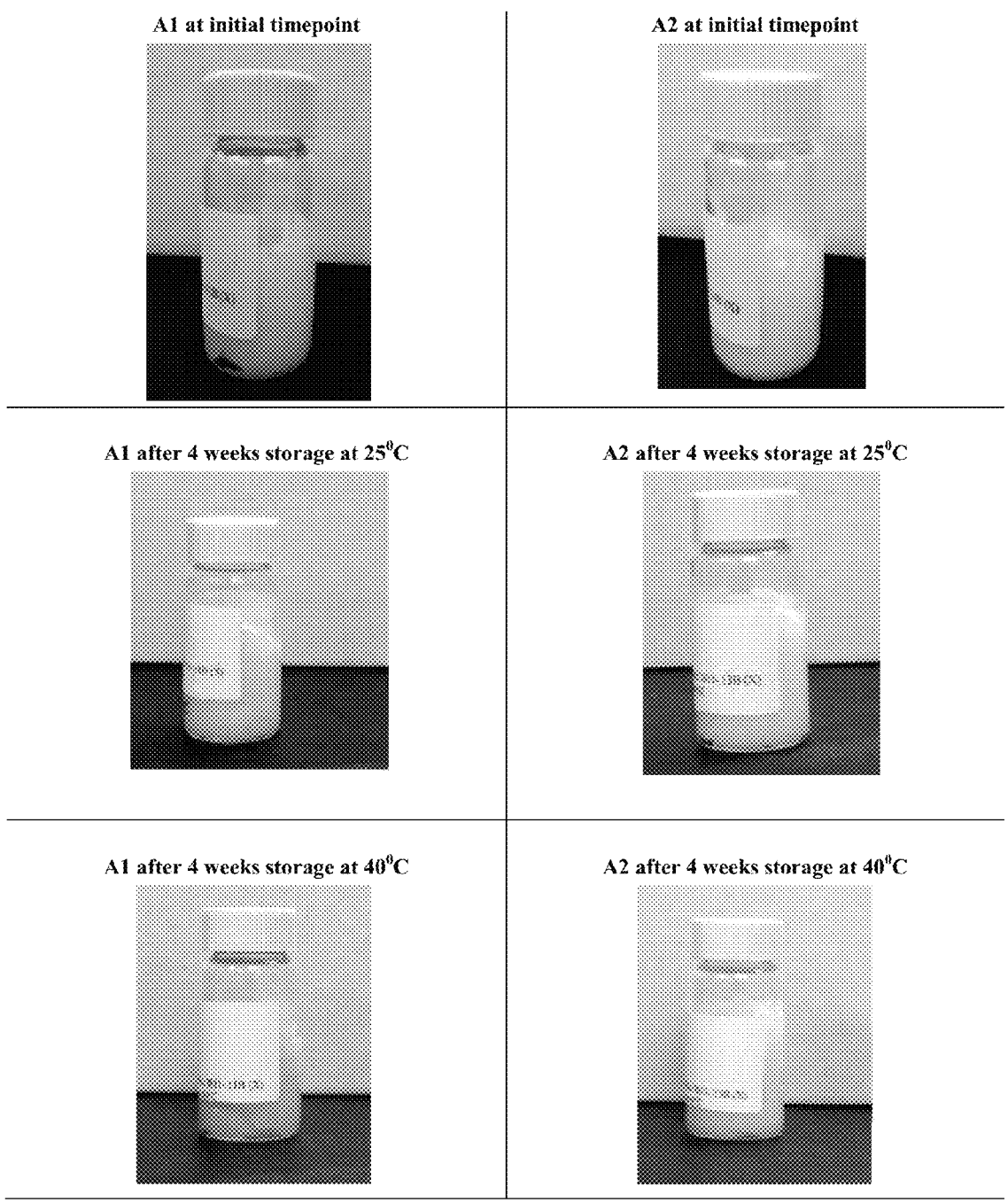
Figure 1. Appearance of formulations following 4 weeks of storage

Figure 2. Polarized light images of dapsone in suspension formulations
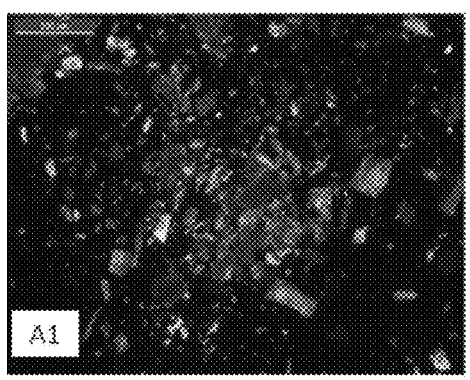
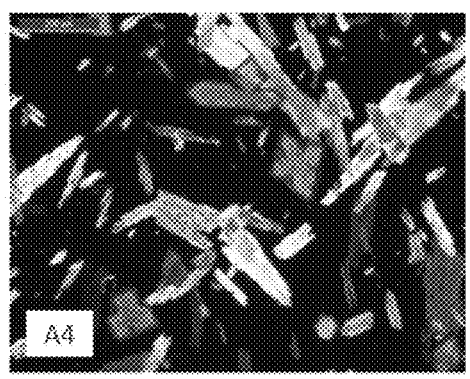
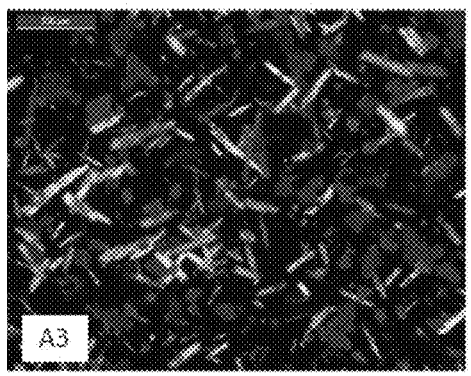
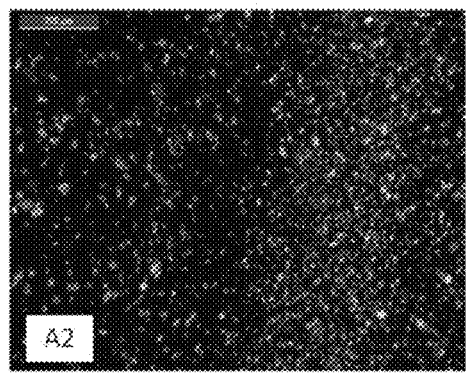

Figure 3. Appearance of formulations with antioxidants or chelating agents over 4 weeks
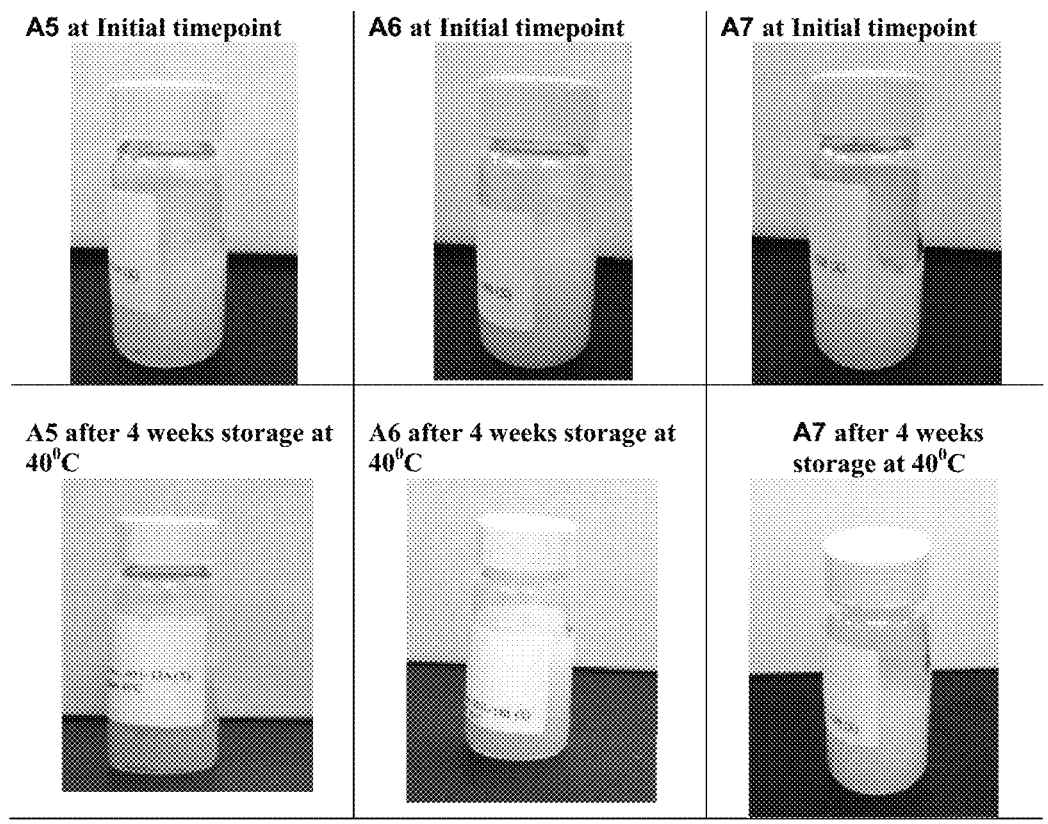

TOPICAL DAPSONE AND DAPSONE/ADAPALENE COMPOSITIONS AND METHODS FOR USE THEREOF

CROSS REFERENCE TO RELATED APPLICATIONS

This application is a divisional of copending U.S. patent application Ser. No. 14/082,955, filed on Nov. 18, 2013, which claims the benefit of U.S. Provisional Application Ser. No. 61/728,403 filed on Nov. 20, 2012 and U.S. Provisional Application Ser. No. 61/770,768 filed on Feb. 28, 2013, all of which are incorporated by reference herein in their entirety.

FIELD

The present embodiments relate generally to compositions useful for treating a variety of dermatological conditions. In particular, some embodiments relate to dapsone and dapsone/adapalene compositions and methods for use thereof.

BACKGROUND

Acne is a group of common skin conditions characterized by the so-called "acneiform" or acne-like skin eruptions, which can be contaminated with bacteria, such as *Propionibacterium acnes*, and can also be marked by inflammation. Acne tends to occur in the areas of skin where the sebaceous glands are most active, such as the face. Acne is associated with psychological trauma, and, if left untreated, can lead to scar formation and disfigurement.

Classification and the diagnosis of various acne conditions can be complex, and even contradictory. Given this complexity and unpredictability, medication and other therapies, are often developed on a trial-and-error basis in order to determine the most effective course of treatment for a particular patient. The outcome of any particular acne treatment regimen greatly varies from patient to patient, as well as throughout treatment of a particular patient. In addition to the complexity and variability of acne conditions, treatment efficacy can be greatly affected by a patient's compliance with the treatment regimen. Patient compliance during acne treatment may be influenced by side effects, which, for topical medications, commonly include redness, itching, and skin peeling. The complexity of the drug regimen can also negatively affect patient compliance, particularly where two or more different topical medications are prescribed simultaneously. Another factor that negatively affects patient compliance is the cost of a drug regiment, which is considerably higher when multiple medications are prescribed. In some countries, acne is considered a cosmetic problem, and acne treatments are not covered by insurance plans, thus further increasing patient's treatment costs. Certain compositions for treatment of acne are available. Many of the available compositions include one active agent known to have anti-acne activity. Stability of compositions with multiple anti-acne agents can be problematic. Also, these compositions can be difficult to manufacture.

The problems described above are not confined to the treatment or acne, but are also applicable to a variety of other skin conditions, including, but not limited, to conditions or classes of conditions with complex or unknown etiology and that are difficult to classify or diagnose, in which, nevertheless, topical application of agents are known to be effective at least in some cases. Examples of such conditions or classes of conditions include psoriasis, rosacea and ichthyosis.

Accordingly, there is a continuing need for compositions and methods used in a treatment of a variety of skin conditions, such as acne, in which topical application is potentially effective. The compositions and methods provided herein address these and other needs in the art.

SUMMARY

Dapsone, (4,4'-diaminodiphenyl sulfone) is a medicament possessing several beneficial medicinal activities. Dapsone is typically administered as one of the medicinal agents used in the treatment of leprosy. Dapsone and its derivatives are also effective for treatment of bacterial infections, protozoal infections such as malaria, *pneumocystis carinii*, and plasmonic infections such as toxoplasmosis.

Dapsone is also useful as an anti-inflammatory agent. It has been used to treat skin diseases characterized by the abnormal infiltration of neutrophils, such as Dermatitis herpetiformis, linear IgA dermatosis, pustular psoriasis, pyoderma gangrenosum, acne vulgaris, and Sweet's Syndrome.

Use of topical compositions of dapsone can be problematic. Topical compositions may act as drying agents for the skin. They remove essential oils and natural skin softeners from the skin thus causing it to be dry, itch and crack. Inclusion of exogenous skin emollients, oils and the like, however, causes phase separation and precipitation of dapsone. Use of typical emulsifiers does not solve the dapsone precipitation owing to the lowered dapsone solubility and conflicting physical characteristics of the phases of the resulting composition. In particular, topical compositions including dapsone and methods are needed that would, for example, exhibit improved effectiveness, reduced side effects, or both, when used in a particular patient with a skin condition. Such improved topical compositions including dapsone and methods of their uses are also needed to improve treatment of patients with acne or suspected acne. The present dapsone and dapsone/adapalene compositions can be useful for treating a variety of dermatological conditions. Some useful compositions include dapsone and/or adapalene in a polymeric viscosity builder. Some compositions can be adjusted to optimize the dermal delivery profile of dapsone to effectively treat dermatological conditions and improve the efficiency of pharmaceutical products applied to the skin. Diethylene glycol monoethyl ether is a solubilizer for dapsone, thereby allowing compositions to be prepared with increased solubilized concentrations of dapsone. As a result, the compositions described herein are effective in treating dermatological conditions in a subject in need thereof.

Moreover, it has been found that use of a polymeric viscosity builder minimizes the intensity of yellowing of the composition caused by the increased solubility of dapsone in diethylene glycol monoethyl ether. In addition, the polymeric viscosity builder influences dapsone crystallization. This, in turn, results in compositions with improved aesthetics (i.e., reduction in particle size which minimizes "gritty" feeling upon application).

In one embodiment, there are provided compositions including dapsone, a first solubilizing agent which is diethylene glycol monoethyl ether, optionally at least one second solubilizing agent, a polymeric viscosity builder, and water, wherein the dapsone is present at a concentration of about 5% w/w to about 10% w/w.

In one embodiment, there are provided compositions including dapsone, a first solubilizing agent which is diethylene glycol monoethyl ether, optionally at least one second solubilizing agent, a polymeric viscosity builder, and water, wherein the dapsone is present at a concentration of about 3% w/w to 8% w/w.

In another embodiment, there are provided methods for treating a dermatological condition. Such methods can be performed, for example, by administering to a subject in need thereof a therapeutically effective amount of a pharmaceutical composition described herein.

BRIEF DESCRIPTION OF THE FIGURES

FIG. 1 presents the impact of an acrylamide/sodium acryloyldimethyltaurate copolymer emulsion viscosity builder on color change.

FIG. 2 presents the impact of an acrylamide/sodium acryloyldimethyltaurate copolymer emulsion viscosity builder on dapsone crystal growth.

FIG. 3 presents the impact of anti-oxidants and chelating agents on color change.

DETAILED DESCRIPTION

It is to be understood that both the foregoing general description and the following detailed description are exemplary and explanatory only and do not restrict the claims. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Some embodiments include compositions and products for treatment of skin conditions and methods of treating skin conditions. The term "skin condition" as used herein encompasses human and animal conditions, disorders, or diseases affecting skin. Such skin conditions include, but are not limited to, conditions involving skin inflammation, conditions involving sebaceous glands and hair follicles, conditions characterized by acneiform symptoms, and conditions involving skin dryness, skin thickening, skin scaling or skin flaking. Skin conditions that can be treated using some compositions, products and methods described herein include, but are not limited to, acne, rosacea, folliculitis, perioral dermatitis, photodamage, skin aging, psoriasis, ichthyosis, atopic dermatitis, treatment of chronic wounds, bed sores, keratosis pilaris scars, including surgical and acne scars, sebaceous cysts, inflammatory dermatoses, post inflammatory hyperpigmentation, eczema, xerosis, pruritus, lichen planus, nodular prurigo, eczema, and miliaria.

The term "acne," as used herein, encompasses skin conditions involving acneiform or acne-like symptoms. For example, a skin condition characterized by follicular eruptions, such as papules and pustules resembling acne, can be categorized as acne. It is to be understood that the term "acne" is not to be limited to diseases and conditions characterized by papules and pustules, but can be characterized by a variety of symptoms. It is also to be understood that a particular patient having acne can be in remission, or the patient's acne can be controlled by continuing treatments, and therefore the patient can exhibit reduced symptoms or be asymptomatic. Nevertheless, continuing treatment of acne can be recommended in such a patient in order to reduce the probability of the return of the acne symptoms.

Symptoms of acne or acne-like conditions include, but are not limited to, the appearance of various skin lesions. The term "lesion" is generally used to denote an infected or diseased patch of skin. A lesion can involve an infected sebaceous gland. Some lesions are more severe than others. Examples of skin lesions are comedones, macules, papules, pustules, nodules and cysts. The term "comedo" (plural "comedones") is used to describe a sebaceous follicle plugged with dirt, other cells, tiny hairs, or bacteria. Comedones include the so-called "blackheads," which can also refer to as "open comedones," which have a spot or a surface that appears black. Comedones also include slightly inflamed, skin colored bumps, as well as "whiteheads," which have a spot or a surface that appears white. The term "macule" generally refers to a flat spot or area of the skin with a changed color, such as a red spot. The term "pustule" is generally used to refer to an inflamed, pus-filled lesion, or a small inflamed elevation of the skin that is filled with pus. The term "papule" is generally used to refer to a small, solid, usually inflammatory elevation of the skin that does not contain pus. The term "nodule" is generally used to refer to an elevation of a skin that is similar to a papule but is white and dome-shaped. Colloquially, a papule, a pustule or a nodule can be referred to as "a pimple" or "a zit." The term "cyst" generally refers to an abnormal membranous sac containing a liquid or semi-liquid substance containing white blood cells, dead cells, and bacteria. Cysts can be painful and extend to deeper layers of skin.

In dermatological science and dermatological and cosmetology practice, acne can be classified or categorized into one or more types or categories, according to one or more lines of categorization, such as a predominantly observed type of symptoms, severity of condition or predominant localization. It is to be understood that classification of acne into one of the subtypes does not mean that the characteristics of the classified condition are limited to the symptoms associated with the specific type.

Comedonal acne is characterized by the appearance of non-inflammatory lesions, such as blackheads and whiteheads. Localized cystic acne is characterized by appearance of a few cysts on face, chest and back. Diffuse cystic acne is characterized by the appearance of cysts on wide areas of face, chest and back. Nodular acne is characterized by the appearance of nodules. Nodulocystic acne is characterized by appearance of nodules and cysts. Acne vulgaris is a common form of acne characterized by the appearance of several types of lesions, which may appear together or separately. Individual acne lesions usually last less than two weeks but the deeper papules and nodules may persist for months. Acne vulgaris commonly affects adolescents, but it may also appear, persist or become more severe in adulthood. Acne vulgaris may occur on the face, chest, back and sometimes even more extensively.

Depending on severity, acne can be mild, moderate or severe. Mild acne is generally categorized by the appearance of with blackheads and whiteheads, but can also include papules and pustules. Moderate acne is generally characterized by appearance of more painful, deep-rooted, inflamed lesions, which can result in scarring. Severe acne is characterized by the appearance of deep-rooted inflammatory lesions, including cysts and nodules which can be painful and can produce scarring. Acne conglobata is a category of acne characterized by highly inflammatory cysts that communicate under the skin with abscesses and burrowing sinus tracts.

Some other skin conditions exhibiting acne-like symptoms which can be treated by the compositions and methods described herein are discussed below. Pyoderma faciale, also known as rosacea fulminans, is a condition that appears in females and is characterized by abrupt appearance of inflamed cysts and nodules localized on the face. Rosacea, which can be referred to as acne rosacea, is a condition that can affects both the skin and the eyes and is characterized by redness, bumps, pimples, and, in advanced stages, thickened skin on the nose. In some classification systems, rosacea and acne are considered as separate conditions. Rosacea usually occurs on the face, although the neck and upper chest are also sometimes involved. A mild degree of eye (ocular) involvement occurs in more than fifty percent of people with rosacea. Perioral dermatitis is characterized by the appearance of small tiny papules, pustules, red bumps and scaling with intense itching. It is usually localized to the surrounding area of the mouth and on the chin, or extends to involve the eyelids and the forehead. Gram-negative folliculitis is a bacterial infection characterized by the appearance of pustules and cysts, possibly occurring as a complication resulting from a long term antibiotic treatment of acne vulgaris.

As used herein, the terms "treatment" or "treating" in reference to a skin condition generally mean "having positive effect on a skin condition" and encompass alleviation of at least one symptom of a skin condition, a reduction in the severity of the skin conditions, or delay, prevention, or inhibition of the progression of the skin condition. Treatment need not mean that the condition is totally cured. A composition or a product useful for treatment of a skin condition, or a method of treating a skin condition, needs only to reduce the severity of a skin condition, reduce the severity of symptoms associated therewith, provide improvement to a patient's quality of life, or delay, prevent, or inhibit the onset of symptoms of a skin condition.

In one embodiment, there are provided compositions including dapsone, a first solubilizing agent which is diethylene glycol monoethyl ether, optionally at least one second solubilizing agent, a polymeric viscosity builder, and water, wherein the dapsone is present at a concentration of about 5% w/w to about 10% w/w, about 1% w/w to about 10% w/w, about 3% w/w to about 10% w/w, about 3% w/w to about 8% w/w, about 4% w/w to about 6% w/w, or about 5%. In certain embodiments, dapsone is present in the composition at 5.0%, 5.5%, 6.0%, 6.5%, 7.0%, 7.5%, 8.0%, 8.5%, 9.0%, 9.5%, or 10.0% w/w.

In some embodiments, the polymeric viscosity builder is an acrylamide/sodium acryloyldimethyltaurate copolymer, and further includes isohexadecane, sorbitan oleate, water, and Polysorbate 80. In some embodiments, the polymeric viscosity builder is present at a concentration of about 2% w/w to about 6% w/w. In some embodiments, the polymeric viscosity builder is present at a concentration of about 3% w/w to about 5% w/w. In some embodiments, the polymeric viscosity builder is present in the composition at about 4% w/w.

In some embodiments, diethylene glycol monoethyl ether is present at a concentration of about 25% w/w to about 40% w/w. In some embodiments, diethylene glycol monoethyl ether is present at a concentration of about 30% w/w to about 40% w/w. In some embodiments, diethylene glycol monoethyl ether is present at a concentration of about 35% w/w to about 40% w/w.

In some embodiments, diethylene glycol monoethyl ether is present at a concentration of about 10% w/w to about 40% w/w, about 20% w/w to about 30% w/w, or about 25%.

In another embodiment, there are provided compositions further including adapalene. In some embodiments, adapalene is present at a concentration of about 0.1% w/w to about 0.3% w/w.

In some embodiments, the second solubilizing agent is selected from alcohols, glycols, esters, ethers, or silicones. Such second solubilizing agents include, but are not limited to, PEG 400, lactic acid, dimethyl isosorbide, propylene glycol, propylene carbonate, hexylene glycol, isostearyl alcohol, benzyl alcohol, diethyl sebacate, and ethanol.

In certain embodiments, the second solubilizing agent is propylene glycol. In some embodiments, propylene glycol is present at a concentration of about 2% w/w to 8% w/w. In some embodiments, propylene glycol is present at a concentration of about 3% w/w to 7% w/w. In some embodiments, propylene glycol is present in the composition at about 5% w/w.

In certain embodiments, the second solubilizing agent is propylene carbonate. In some embodiments, propylene carbonate is present at a concentration of about 2% w/w to 8% w/w. In some embodiments, propylene carbonate is present at a concentration of about 3% w/w to 7% w/w. In some embodiments, propylene carbonate is present in the composition at about 5% w/w.

In certain embodiments, the second solubilizing agent is ethanol. In some embodiments, ethanol is present at a concentration of about 1% w/w to about 5% w/w. In some embodiments, ethanol is present at a concentration of about 2% w/w to about 4% w/w. In some embodiments, ethanol is present in the composition at about 3% w/w.

In some embodiments, the compositions further include methyl paraben.

In other embodiments, the compositions further include carbomer homopolymer type C. In some embodiments, carbomer homopolymer type C is present at a concentration of about 0.7% w/w to about 1.5% w/w. In other embodiments, carbomer homopolymer type C is present at a concentration of about 0.85% w/w to about 1.0% w/w.

In some embodiments, the compositions further include a neutralizing agent. In certain embodiments, the neutralizing agent is an ionic or amine buffer. In certain embodiments, the neutralizing agent is sodium hydroxide or triethanolamine. Use of a neutralizing agent results in compositions typically having a pH from 5.5 to 6.5.

In some embodiments, the compositions further include a chelating agent. In some embodiments, the chelating agent is ethylene diamine tetraacetic acid (EDTA). EDTA is typically present in the compositions from about 0.02% w/w to about 0.04% w/w. In certain embodiments, EDTA is present in the compositions at about 0.03% w/w.

Compositions described herein are typically in the form of a gel, an emulsion, a cream, a liquid, a paste, a lotion, a nanoemulsion, a microemulsion, a reverse emulsion, or a liposomal cream.

EMBODIMENTS

The following embodiments are specifically contemplated herein.

Embodiment 1

A composition comprising dapsone, a first solubilizing agent which is diethylene glycol monoethyl ether, optionally at least one second solubilizing agent, a polymeric viscosity builder, and water, wherein the dapsone is present in the composition at a concentration of about 3% w/w to about 10% w/w.

Embodiment 2

The composition of embodiment 1, wherein the diethylene glycol monoethyl ether is present at a concentration of about 10% w/w to about 40% w/w.

Embodiment 3

The composition of embodiment 1, wherein the diethylene glycol monoethyl ether is present at a concentration of about 20% w/w to about 30% w/w.

Embodiment 4

The composition of embodiment 1, wherein the diethylene glycol monoethyl ether is present in the composition at a concentration of about 25% w/w.

Embodiment 5

The composition of embodiment 1, further comprising adapalene.

Embodiment 6

The composition of embodiment 5, wherein the adapalene is present at a concentration of about 0.1% w/w to about 0.3% w/w.

Embodiment 7

The composition of embodiment 1 wherein the second solubilizing agent is selected an alcohol, a glycol, an ester, or an ether.

Embodiment 8

The composition of embodiment 1, wherein the second solubilizing agent is PEG 400, lactic acid, dimethyl isosorbide, propylene glycol, propylene carbonate, hexylene glycol, isostearyl alcohol, diethyl sebacate, or ethanol.

Embodiment 9

The composition of embodiment 8, wherein the second solubilizing agent is propylene glycol.

Embodiment 10

The composition of embodiment 9, wherein the propylene glycol is present in the composition at a concentration of about 5% w/w.

Embodiment 11

The composition of embodiment 8, wherein the second solubilizing agent is propylene carbonate.

Embodiment 12

The composition of embodiment 11, wherein the propylene carbonate is present in the composition at a concentration of about 5% w/w.

Embodiment 13

The composition of embodiment 8, wherein the second solubilizing agent is ethanol.

Embodiment 14

The composition of embodiment 13, wherein the ethanol is present in the composition at a concentration of about 3% w/w.

Embodiment 15

The composition of embodiment 1, wherein the polymeric viscosity builder comprises an acrylamide/sodium acryloyldimethyltaurate copolymer.

Embodiment 16

The composition of embodiment 1, wherein the polymeric viscosity builder is present at a concentration of about 2% w/w to about 6% w/w.

Embodiment 17

The composition of embodiment 1, wherein the polymeric viscosity builder is present at a concentration of about 4% w/w.

Embodiment 18

The composition of embodiment 1, further comprising methyl paraben.

Embodiment 19

The composition of embodiment 1, further comprising Carbomer interpolymer type A, Carbomer interpolymer type B, or Carbomer Homopolymer Type C.

Embodiment 20

The composition of embodiment 19, wherein the Carbomer Homopolymer Type C is present at a concentration of about 0.7% w/w to about 1.5% w/w.

Embodiment 21

The composition of embodiment 19, wherein the Carbomer Homopolymer Type C is present at a concentration of about 0.85% w/w to about 1.5% w/w.

Embodiment 22

The composition of embodiment 19, wherein the Carbomer interpolymer Type A is present at a concentration of about 1% w/w to about 2% w/w.

Embodiment 23

The composition of embodiment 19, wherein the Carbomer interpolymer Type B is present at a concentration of about 0.1% w/w to about 0.5% w/w.

Embodiment 24

The composition of embodiment 1, further comprising a neutralizing agent.

Embodiment 25

The composition of embodiment 24 wherein the neutralizing agent is NaOH or triethanolamine.

Embodiment 26

The composition of embodiment 1 further comprising a chelating agent.

Embodiment 27

The composition of embodiment 26, wherein the chelating agent is ethylene diamine tetraacetic acid.

Embodiment 28

The composition of embodiment 27, wherein the ethylene diamine tetraacetic acid is present at a concentration of about 0.02% w/w to about 0.04% w/w.

Embodiment 29

The composition of embodiment 27, wherein the ethylene diamine tetraacetic acid is present in the composition at about 0.03% w/w.

Embodiment 30

The composition of embodiment 1 wherein the composition is in the form of a gel, a suspension, an emulsion, a cream, a liquid, a paste, a lotion, a nanoemulsion, a microemulsion, a reverse emulsion, or a liposomal cream.

Embodiment 31

A method for treating a dermatological condition comprising administering to a subject in need thereof a therapeutically effective amount of a composition of embodiment 1.

Embodiment 32

The method of embodiment 31 wherein the condition is acne vulgaris, rosacea, atopic dermatitis, treatment of chronic wounds, bed sores, keratosis pilaris, sebaceous cysts, inflammatory dermatoses, post inflammatory hyperpigmentation, eczema, xerosis, pruritus, lichen planus, nodular prurigo, dermatitis, eczema, or miliaria.

Embodiment 33

The method of embodiment 32 wherein the condition is acne vulgaris.

Embodiment 34

The composition of embodiment 1, 2, 3, or 4, further comprising adapalene.

Embodiment 35

The composition of embodiment 34, wherein the adapalene is present at a concentration of about 0.1% w/w to about 0.3% w/w.

Embodiment 36

The composition of embodiment 1, 2, 3, 4, 34, or 35, wherein the second solubilizing agent is selected an alcohol, a glycol, an ester, or an ether.

Embodiment 37

The composition of embodiment 1, 2, 3, 4, 34, 35, or 36, wherein the second solubilizing agent is PEG 400, lactic acid, dimethyl isosorbide, propylene glycol, propylene carbonate, hexylene glycol, isostearyl alcohol, diethyl sebacate, or ethanol.

Embodiment 38

The composition of embodiment 37, wherein the second solubilizing agent is propylene glycol.

Embodiment 39

The composition of embodiment 38, wherein the propylene glycol is present in the composition at a concentration of about 5% w/w.

Embodiment 40

The composition of embodiment 37, wherein the second solubilizing agent is propylene carbonate.

Embodiment 41

The composition of embodiment 40, wherein the propylene carbonate is present in the composition at a concentration of about 5% w/w.

Embodiment 42

The composition of embodiment 37, wherein the second solubilizing agent is ethanol.

Embodiment 43

The composition of embodiment 42, wherein the ethanol is present in the composition at a concentration of about 3% w/w.

Embodiment 44

The composition of embodiment 1, 2, 3, 4, 34, 35, 36, 37, 38, 39, 40, 41, 42, or 43, wherein the polymeric viscosity builder comprises an acrylamide/sodium acryloyldimethyltaurate copolymer.

Embodiment 45

The composition of embodiment 1, 2, 3, 4, 34, 35, 36, 37, 38, 39, 40, 41, 42, 43, or 44, wherein the polymeric viscosity builder is present at a concentration of about 2% w/w to about 6% w/w.

Embodiment 46

The composition of embodiment 45, wherein the polymeric viscosity builder is present at a concentration of about 4% w/w.

Embodiment 47

The composition of embodiment 1, 2, 3, 4, 34, 35, 36, 37, 38, 39, 40, 41, 42, 43, 44, 45, or 46, further comprising methyl paraben.

Embodiment 48

The composition of embodiment 1, 2, 3, 4, 34, 35, 36, 37, 38, 39, 40, 41, 42, 43, 44, 45, 46, or 47, further comprising Carbomer interpolymer type A, Carbomer interpolymer type B, or Carbomer Homopolymer Type C.

Embodiment 49

The composition of embodiment 48, wherein the Carbomer Homopolymer Type C is present at a concentration of about 0.7% w/w to about 1.5% w/w.

Embodiment 50

The composition of embodiment 48, wherein the Carbomer Homopolymer Type C is present at a concentration of about 0.85% w/w to about 1.5% w/w.

Embodiment 51

The composition of embodiment 48, wherein the Carbomer interpolymer Type A is present at a concentration of about 1% w/w to 2% w/w.

Embodiment 52

The composition of embodiment 48, wherein the Carbomer interpolymer Type B is present at a concentration of about 0.1% w/w to about 0.5% w/w.

Embodiment 53

The composition of embodiment 1, 2, 3, 4, 34, 35, 36, 37, 38, 39, 40, 41, 42, 43, 44, 45, 46, 47, 48, 49, 50, 51, or 52, further comprising a neutralizing agent.

Embodiment 54

The composition of embodiment 53 wherein the neutralizing agent is NaOH or triethanolamine.

Embodiment 55

The composition of embodiment 1, 2, 3, 4, 34, 35, 36, 37, 38, 39, 40, 41, 42, 43, 44, 45, 46, 47, 48, 49, 50, 51, 52, 53, or 54, further comprising a chelating agent.

Embodiment 56

The composition of embodiment 55, wherein the chelating agent is ethylene diamine tetraacetic acid.

Embodiment 57

The composition of embodiment 56, wherein the ethylene diamine tetraacetic acid is present at a concentration of about 0.02% w/w to about 0.04% w/w.

Embodiment 58

The composition of embodiment 56, wherein the ethylene diamine tetraacetic acid is present in the composition at about 0.03% w/w.

Embodiment 59

The composition of embodiment 1, 2, 3, 4, 34, 35, 36, 37, 38, 39, 40, 41, 42, 43, 44, 45, 46, 47, 48, 49, 50, 51, 52, 53, 54, 55, 56, 57, or 58, wherein the composition is in the form of a gel, a suspension, an emulsion, a cream, a liquid, a paste, a lotion, a nanoemulsion, a microemulsion, a reverse emulsion, or a liposomal cream.

Embodiment 60

A method for treating a dermatological condition comprising administering to a subject in need thereof a therapeutically effective amount of a composition of embodiment 1, 2, 3, 4, 34, 35, 36, 37, 38, 39, 40, 41, 42, 43, 44, 45, 46, 47, 48, 49, 50, 51, 52, 53, 54, 55, 56, 57, 58, or 59.

Embodiment 61

The method of embodiment 60 wherein the condition is acne vulgaris, rosacea, atopic dermatitis, treatment of chronic wounds, bed sores, keratosis pilaris, sebaceous cysts, inflammatory dermatoses, post inflammatory hyperpigmentation, eczema, xerosis, pruritus, lichen planus, nodular prurigo, dermatitis, eczema, or miliaria.

Embodiment 62

The method of embodiment 60 wherein the condition is acne vulgaris.

The following examples are intended only to illustrate the some embodiments and should in no way be construed as limiting the claims.

EXAMPLES

Example 1

Table 1 lists two formulations (containing equivalent levels of diethylene glycol monoethyl ether) that show the impact of acrylamide/sodium acryloyldimethyltaurate copolymer based thickener on dapsone particle size. FIG. 2 presents impact of acrylamide/sodium acryloyldimethyltaurate copolymer based thickener on dapsone crystal growth. The microscopic image of ENA (30% diethylene glycol monoethyl ether, 4% acrylamide/sodium acryloyldimethyltaurate copolymer based thickener) in comparison to ENC (30% diethylene glycol monoethyl ether, 1% Carbopol 980) shows a clear difference in particle size of the dapsone. Larger crystals were observed in the sample with carbomer homopolymer type C (ENC vs. ENA).

TABLE 1

| Formulations Tested For Dapsone Crystal Size | | |
|---|---|---|
| Formulation # | ENA | ENC |
| Dapsone | 7.5 | 7.5 |
| Diethylene glycol monoethyl ether | 30 | 30 |
| Carbomer homopolymer type C. | — | 1 |

TABLE 1-continued

Formulations Tested For Dapsone Crystal Size

| Formulation # | ENA | ENC |
|---|---|---|
| acrylamide/sodium acryloyldimethyltaurate copolymer based thickener | 4 | — |
| Methyl paraben | 0.2 | 0.2 |
| pH adjusting solution | pH 5.5-7 | pH 5.5-7 |
| Purified Water | Q.S 100 | Q.S 100 |

Example 2

Example compositions contemplated for use as described herein are set forth in Table 2 below:

TABLE 2

| Composition # | 1 | 2 | 3 | 4 | 5 | 6 | 7 | 8 | 9 | 10 |
|---|---|---|---|---|---|---|---|---|---|---|
| Dapsone | | | | | 5-10 | | | | | |
| Adapalene | | | — | | | | 0.1-0.3 | | | |
| Diethylene glycol monoethyl ether | 30 | 35 | 40 | 30 | 35 | 30 | 35 | 40 | 30 | 35 |
| Carbomer homopolymer type C | — | | 0.85-1.5 | — | — | — | 0.85-1.5 | | | |
| Acrylamide/sodium acryloyldimethyltaurate copolymer emulsion | 4 | | — | | | 4 | | | — | |
| Methyl paraben | | | | | 0.2 | | | | | |
| NaOH/pH adjusting solution | | | | | pH 5.5-6.5 | | | | | |
| Purified Water | | | | | Q.S 100 | | | | | |

Example 3

Anti-oxidants and chelating agents such as sodium metabisulfite, citric acid and EDTA were added to formulations to help slow down or completely stop any impurity formation. Table 3 presents the composition of formulations tested. Formulation A7 with sodium metabisulfite minimized the intensity of yellow color caused by the increased solubility of dapsone in diethylene glycol monoethyl ether and maintained the low color intensity over time at accelerated condition (40° C.). See FIG. 3 for appearance of the formulations over 4 weeks. Table 4 presents the formulation panel summarizing other formulation options with chelating agents and antioxidants.

TABLE 3

Compositions Tested containing Antioxidants or Chelating Agents

| Composition # | A5 | A6 | A7 |
|---|---|---|---|
| Dapsone | | 7.5 | |
| Diethylene glycol monoethyl ether | 35 | 40 | 35 |
| carbomer homopolymer type C | 1.25 | — | 1.25 |
| Acrylamide/sodium acryloyldimethyltaurate copolymer emulsion | — | 4 | — |
| EDTA | 0.05 | | |
| Anhydrous Citric Acid | 0.1 | | |
| Sodium Metabisulfite | — | | 0.2 |
| Methyl paraben | 0.17 | | 0.2 |
| Propyl paraben | 0.03 | | — |
| NaOH/pH adjusting solution | | pH 5.5-6.5 | |
| Purified Water | | Q.S 100 | |

TABLE 4

Formulation panel summarizing other formulation options

| Composition # | 1 | 2 | 3 | 4 | 5 | 6 | 7 | 8 | 9 | 10 |
|---|---|---|---|---|---|---|---|---|---|---|
| Dapsone | | | | | 5-10 | | | | | |
| Adapalene | | | — | | | | 0.1-0.3 | | | |
| Diethylene glycol monoethyl ether | 30 | 35 | 40 | 30 | 35 | 30 | 35 | 40 | 30 | 35 |
| carbomer homopolymer type C | — | | 0.85-1.5 | — | | | 0.85-1.5 | | | |
| Acrylamide/sodium Acryloyl-dimethyltaurate copolymer emulsion | 4 | | — | 4 | | — | | | | |
| EDTA | | | | | 0-0.1 | | | | | |
| Citric Acid | | | | | 0-0.1 | | | | | |
| Sodium Metabisulfite | | | | | 0-0.5 | | | | | |
| Methyl paraben | | | | | 0.2 | | | | | |
| NaOH/pH adjusting solution | | | | | pH 5.5-6.5 | | | | | |
| Purified Water | | | | | Q.S 100 | | | | | |

Example 4

Additional example compositions contemplated for use as described herein are set forth in Table 5 below.

TABLE 5

Additional examples containing alternate neutralizer

| | % w/w | | | | | |
|---|---|---|---|---|---|---|
| Materials | 5-1 | 5-2 | 5-3 | 5-4 | 5-5 | 5-6 |
| Dapsone | | | 7.5 | | | |
| Adapalene | | — | | | 0.3 | — |
| Diethylene glycol monoethyl ether | 30 | 35 | 40 | 30 | 40 | 25 |
| carbomer homopolymer type C | | | 1 | | | |
| Methylparaben | | | 0.2 | | | |
| Triethanolamine (TEA) Q.S. | | | pH 5.5-6.5 | | | |
| Hydrochloric Acid Q.S | | | pH 5.5-6.5 | | | |
| Purified Water | | | q.s.a.d. 100 | | | |

Example 4

Additional example compositions contemplated for use as described herein are set forth in Table 6 below.

TABLE 6

Additional examples (containing co-solvents, stabilizer and alternate thickener)

| | % w/w | | | | | |
|---|---|---|---|---|---|---|
| Materials | 6-1 | 6-2 | 6-3 | 6-4 | 6-5 | 6-6 |
| Dapsone | 7.5 | 10 | | 7.5 | | |
| Adapalene | — | | | 0.3 | | |
| Diethylene glycol monoethyl ether | 25 | 35 | 35 | 25 | 30 | 40 |
| Propylene glycol | | | | 5 | | |
| Propylene Carbonate | | | 5 | | | |
| Ethanol (absolute) | | 3 | | — | | 3 |
| EDTA | | | 0.03 | | | |
| Carbomer Interpolymer Type A | | | — | | 1.5 | |
| Carbomer Interpolymer Type B | | | — | | 0.3 | |
| Acrylamide/sodium acryloyldimethyltaurate copolymer emulsion | | | 4 | | — | 4 |
| Methyl Paraben | | | 0.2 | | | |
| Triethanolamine | | | — | | Q.S. pH 5.5-6.5 | |
| Purified Water | | | q.s.a.d. 100 | | | |

Example 5

Another useful composition is depicted in Table 7.

TABLE 7

| Ingredient | Amount (% w/w) |
| --- | --- |
| Dapsone | 5-8 |
| Adapalene | 0.1-0.3 |
| Diethylene glycol monoethyl ether | 40.00 |
| Propylene glycol | 5.00 |
| Ethanol (absolute) | 3.00 |
| Ethylene Diamine Tetraacetic acid (EDTA) | 0.03 |
| Methyl Paraben | 0.20 |
| Sepineo P 600 | 4.00 |
| Purified Water | Q.S. |

Example 6

Another useful composition is depicted in Table 8.

TABLE 8

| Ingredient | Amount (% w/w) |
| --- | --- |
| Dapsone | 5.0 |
| Diethylene glycol monoethyl ether | 25 |
| Methyl Paraben | 0.2 |
| Carbopol 980 | 0.85 |
| Sodium Hydroxide | 0.2 |
| Purified Water | Q.S. |

While this some embodiments have been described with respect to these specific examples, it is understood that other modifications and variations are possible without departing from the spirit of the invention. Each and every reference identified herein is incorporated by reference in its entirety.

What is claimed is:

1. A method for treating a dermatological condition selected from the group consisting of acne vulgaris and rosacea comprising administering to a subject having the dermatological condition selected from the group consisting of acne vulgaris and rosacea a topical pharmaceutical composition comprising:
   about 7.5% w/w dapsone;
   about 30% w/w to about 40% w/w diethylene glycol monoethyl ether;
   about 2% w/w to about 6% w/w of a polymeric viscosity builder comprising acrylamide/sodium acryloyldimethyl taurate copolymer; and
   water;
   wherein the topical pharmaceutical composition does not comprise adapalene.

2. The method of claim 1, wherein the diethylene glycol monoethyl ether is present at a concentration of about 30% w/w.

3. The method of claim 1, wherein the polymeric viscosity builder is present at a concentration of about 4% w/w.

4. The method of claim 1, wherein the topical pharmaceutical composition further comprises methyl paraben.

5. The method of claim 1 wherein the dermatological condition is acne vulgaris.

6. A method for treating a dermatological condition selected from the group consisting of acne vulgaris and rosacea comprising administering to a subject having the dermatological condition selected from the group consisting of acne vulgaris and rosacea a topical pharmaceutical composition comprising:
   about 7.5% w/w dapsone;
   about 30% w/w diethylene glycol monoethyl ether;
   about 4% w/w of a polymeric viscosity builder comprising acrylamide/sodium acryloyldimethyl taurate copolymer; and
   water;
   wherein the topical pharmaceutical composition does not comprise adapalene.

7. The method of claim 6, wherein the topical pharmaceutical composition further comprises methyl paraben.

8. The method of claim 6 wherein the dermatological condition is acne vulgaris.

* * * * *

(12) INTER PARTES REVIEW CERTIFICATE (2844th)
United States Patent
Warner et al.

(10) Number: US 9,517,219 K1
(45) Certificate Issued: Sep. 26, 2022

(54) TOPICAL DAPSONE AND DAPSONE/ADAPLENE COMPOSITIONS AND METHODS FOR USE THEREOF

(71) Applicants: Kevin S. Warner; Ajay P. Parashar; Vijaya Swaminathan; Varsha Bhatt

(72) Inventors: Kevin S. Warner; Ajay P. Parashar; Vijaya Swaminathan; Varsha Bhatt

(73) Assignee: ALMIRALL, LLC

Trial Numbers:

IPR2019-00207 filed Nov. 6, 2018
IPR2019-01095 filed Jun. 7, 2019

Inter Partes Review Certificate for:

Patent No.: 9,517,219
Issued: Dec. 13, 2016
Appl. No.: 14/885,805
Filed: Oct. 16, 2015

The results of IPR2019-00207 joined with IPR2019-01095 are reflected in this inter partes review certificate under 35 U.S.C. 318(b).

INTER PARTES REVIEW CERTIFICATE
U.S. Patent 9,517,219 K1
Trial No. IPR2019-00207
Certificate Issued Sep. 26, 2022

AS A RESULT OF THE INTER PARTES REVIEW PROCEEDING, IT HAS BEEN DETERMINED THAT:

Claims 1-8 are cancelled.

\* \* \* \* \*